(12) United States Patent
Tanaka et al.

(10) Patent No.: US 8,436,196 B2
(45) Date of Patent: May 7, 2013

(54) TYPE I NATURAL CERAMIDE DERIVATIVE AND METHOD FOR PRODUCING SAME

(75) Inventors: Tatsuyoshi Tanaka, Takasago (JP); Kazumi Okuro, Osaka (JP)

(73) Assignee: Kaneka Corporation, Osaka (JP)

( * ) Notice: Subject to any disclaimer, the term of this patent is extended or adjusted under 35 U.S.C. 154(b) by 229 days.

(21) Appl. No.: 13/121,094

(22) PCT Filed: Sep. 30, 2009

(86) PCT No.: PCT/JP2009/067008
§ 371 (c)(1),
(2), (4) Date: May 18, 2011

(87) PCT Pub. No.: WO2010/038765
PCT Pub. Date: Apr. 8, 2010

(65) Prior Publication Data
US 2011/0213031 A1    Sep. 1, 2011

(30) Foreign Application Priority Data
Sep. 30, 2008  (JP) ................. 2008-254125

(51) Int. Cl.
*C12Q 1/12*    (2006.01)
*A01N 37/06*    (2006.01)
*A01N 37/02*    (2006.01)

(52) U.S. Cl.
USPC ............................ 554/37; 514/549; 514/552

(58) Field of Classification Search .................... 554/37; 514/549, 552
See application file for complete search history.

(56) References Cited

FOREIGN PATENT DOCUMENTS
JP    8-502961    4/1996
JP    3782102 B2    6/2006

OTHER PUBLICATIONS

English translation of International Preliminary Search Report on Patentability for PCT/JP/067008 dated May 10, 2011.

*Primary Examiner* — Deborah D Carr
(74) *Attorney, Agent, or Firm* — Novak Druce Connolly Bove + Quigg LLP

(57) ABSTRACT

The present invention aims to provide a novel type I natural ceramide derivative having a structure more similar to that of a type I natural ceramide composed of sphingosine and an ω-acyloxy long-chain carboxylic acid; and a method for producing the same. The derivative is provided by reacting an ω-acyloxy long-chain fatty acid derivative with dihydrosphingosine or a salt thereof. The thus produced novel type I natural ceramide derivative, when combined with other ceramides, can significantly improve the compatibility of ceramides, which facilitates preparation of a composition containing ceramides, such as a moisturizer or a cosmetic, and also increases the storage stability of the composition.

20 Claims, No Drawings

TYPE I NATURAL CERAMIDE DERIVATIVE AND METHOD FOR PRODUCING SAME

CROSS REFERENCE TO RELATED APPLICATIONS

This application is a National Phase filing under 35 U.S.C. §371 of PCT/JP2009/067008 filed on Sep. 30, 2009; and this application claims priority to Application No. 2008-254125 filed in Japan on Sep. 30, 2008 under 35 U.S.C. §119; the entire contents of all are hereby incorporated by reference.

TECHNICAL FIELD

The present invention relates to a novel type I natural ceramide derivative and a method for producing the same.

BACKGROUND ART

Type I natural ceramides exist in human skin stratum corneum in a high proportion. The proportion of type I natural ceramides, however, is found to significantly decrease in the stratum corneum of people suffering from, particularly, atopic dermatitis. Type I natural ceramides are a very vital component in maintaining skin homeostasis, and they have been drawing attention as a moisturizer in recent years.

A generally known type I natural ceramide is a compound having a structure represented by the following formula (4):

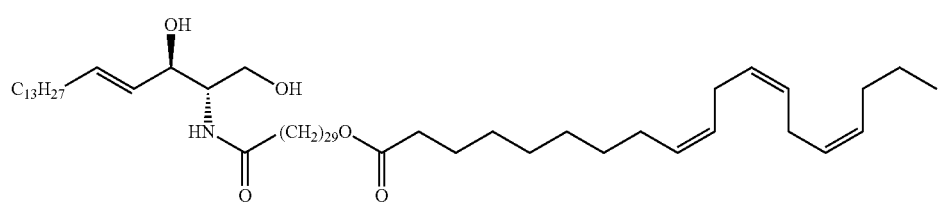

(4)

in which sphingosine is linked to an ω-acyloxy long-chain carboxylic acid via an amide bond (Patent Document 1). Also known in the art is a ceramide derivative composed of phytosphingosine and an ω-acyloxy long-chain carboxylic acid, as represented by the following formula (5).

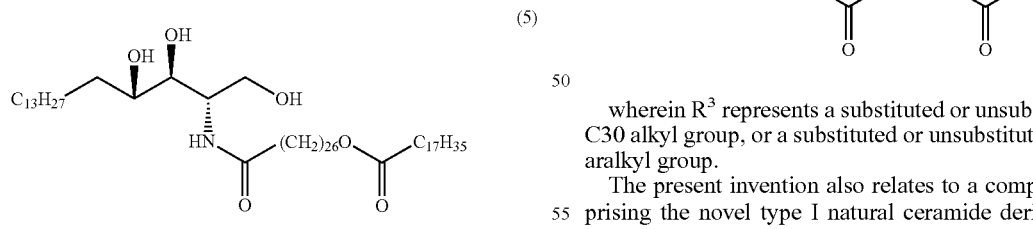

(5)

This derivative has been regarded as a type I natural ceramide (Patent Documents 1 and 2).
Patent Document 1: JP 3782101 B
Patent Document 2: JP H08-502961 T

SUMMARY OF THE INVENTION

Type I natural ceramides are generally known to have a structure represented by the formula (4). This compound, however, is neither easily available nor easily synthesizable. For this reason, the comparatively easily synthesizable compound represented by formula (5), which is composed of phytosphingosine and an ω-acyloxy long-chain carboxylic acid, has been marketed as a type I natural ceramide. However, the compound represented by formula (5) has a different number of hydroxyl groups in the sphingosine skeleton and a different number of carbon atoms in the N-acyl moiety, compared to the type I natural ceramide represented by formula (4). Accordingly, a method has been desired which enables easy synthesis of a type I natural ceramide having a structure more similar to the structure represented by formula (4) at a low cost.

The present invention has an object to provide a novel type I natural ceramide derivative having a structure more similar to the structure represented by formula (4), and a method for producing the same.

As a result of eager examination, the present inventors have found a novel type I natural ceramide derivative having a structure more similar to the structure represented by formula (4), and a method for producing the same.

That is, the present invention relates to a novel type I natural ceramide derivative represented by formula (1):

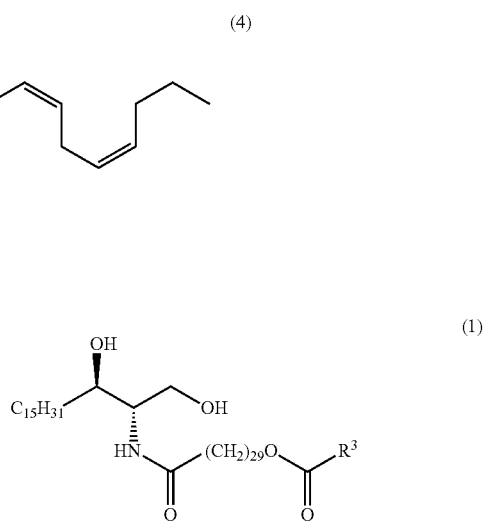

(1)

wherein $R^3$ represents a substituted or unsubstituted C1 to C30 alkyl group, or a substituted or unsubstituted C7 to C20 aralkyl group.

The present invention also relates to a composition comprising the novel type I natural ceramide derivative represented by formula (1).

The present invention also relates to an external preparation for skin, comprising the novel type I natural ceramide derivative represented by formula (1).

Further, the present invention relates to a moisturizer comprising the novel type I natural ceramide derivative represented by formula (1).

Furthermore, the present invention relates to a method for producing the novel type I natural ceramide derivative represented by formula (1), comprising
reacting an ω-acyloxy long-chain fatty acid derivative represented by formula (2):

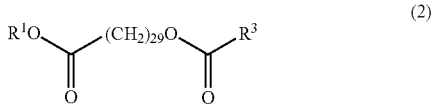

(2)

wherein $R^1$ represents a substituted or unsubstituted C1 to C18 alkyl group, a substituted or unsubstituted C6 to C20 aryl group, a substituted or unsubstituted C7 to C20 aralkyl group, or hydrogen, and $R^3$ is the same as defined above, with dihydrosphingosine represented by formula (3):

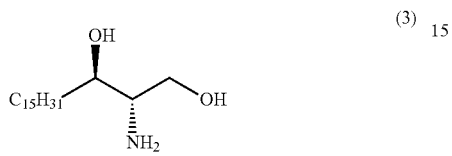

(3)

or a salt thereof.

The method according to the present invention enables easy synthesis of a type I natural ceramide having a structure more similar to that of the type I natural ceramide represented by formula (4). The thus produced novel type I natural ceramide derivative, when combined with other ceramides, can significantly improve the compatibility of ceramides, which facilitates preparation of a composition containing ceramides, such as a moisturizer or a cosmetic, and also increases the storage stability of the composition.

BEST MODE FOR CARRYING OUT THE INVENTION

Hereinafter, the present invention will be described in detail.

First, the novel type I natural ceramide derivative represented by formula (1):

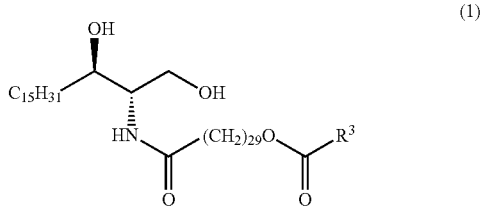

(1)

is described.

In the formula (1), $R^3$ represents a substituted or unsubstituted C1 to C30 alkyl group, or a substituted or unsubstituted C7 to C20 aralkyl group. Examples of a substituent include an alkyl group, an aryl group, an aralkyl group, an amino group, a nitro group, a sulfonyl group, a halogen atom, a hydroxyl group, an acyloxy group, and an alkoxy group.

Examples of the C1 to C30 alkyl group which may be substituted include methyl, ethyl, propyl, isopropyl, isobutyl, tert-butyl, cyclopentyl, cyclohexyl, 1-hydroxypentadecyl, dodecyl, pentadecyl, and heptadecanyl. Also, as a $COR^3$ group formed with an adjacent carbonyl group, examples include octadecanoyl, oleoyl, linoleoyl, and linolenoyl.

Examples of the C7 to C20 aralkyl group which may be substituted include benzyl.

Among these, unsubstituted alkyl groups are preferable. More preferably, the $COR^3$ group formed with an adjacent carbonyl group is an octadecanoyl group, an oleoyl group, a linoleoyl group, or a linolenoyl group. Most preferably, the $COR^3$ group formed with an adjacent carbonyl group is an octadecanoyl group.

Next, the method for producing the novel type I natural ceramide derivative represented by formula (1) is described.

The novel type I natural ceramide derivative represented by formula (1) can be produced by reacting an ω-acyloxy long-chain fatty acid derivative (hereinafter also referred to as "ω-acyloxy long-chain fatty acid derivative (2)") represented by formula (2):

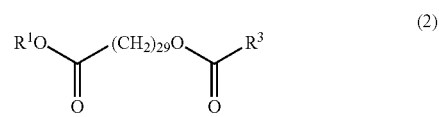

(2)

with dihydrosphingosine represented by formula (3):

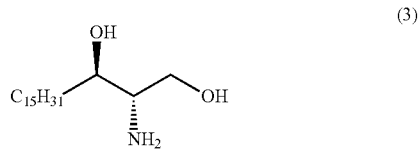

(3)

or a salt thereof.

In the formula (2), $R^1$ represents a substituted or unsubstituted C1 to C18 alkyl group, a substituted or unsubstituted C6 to C20 aryl group, a substituted or unsubstituted C7 to C20 aralkyl group, or hydrogen. Examples of a substituent for $R^1$ include the same substituents mentioned for $R^3$.

Examples of the C1 to C18 alkyl group which may be substituted include methyl, ethyl, propyl, isopropyl, isobutyl, tert-butyl, cyclopentyl, cyclohexyl, pentadecyl, 1-hydroxypentadecyl, and dodecyl.

Examples of the C6 to C20 aryl group which may be substituted include phenyl, p-methoxyphenyl, p-chlorophenyl, p-nitrophenyl, p-trifluoromethylphenyl, p-tolyl, and naphthyl.

Examples of the C7 to C20 aralkyl group which may be substituted include benzyl.

Among these, a methyl group, an ethyl group, a propyl group, an isopropyl group, a phenyl group, a p-nitrophenyl group, a p-trifluorophenyl group, a benzyl group, and hydrogen are preferable, a p-nitrophenyl group and hydrogen are more preferable, and hydrogen is most preferable.

In the formula (2), $R^3$ is the same as defined in the formula (1).

The ω-acyloxy long-chain fatty acid derivative represented by formula (2) can be synthesized by, for example, a method of causing a coupling reaction of a C15 ω-hydroxy long-chain fatty acid derivative synthesized by hydrolysis of pentadecanolide with an enamine derived from cyclododecanone, and then causing a ring-opening reaction and a reduction of ketone (JP 3782102 B); or a method of coupling, in the presence of a copper catalyst, a C15 ω-hydroxy long-chain fatty acid ester derivative synthesized by hydrolysis of pentadecanolide with a Grignard reagent prepared from an ω-hydroxy-α-haloalkane derivative that is synthesized also from pentadecanolide (JP 2618283 B).

The dihydrosphingosine represented by formula (3) may be used having a free amino group, or may be used in the form of a salt at the amino group thereof. Examples of the salt include inorganic salts such as hydrochloride and sulfate, and organic salts such as methanesulfonate, p-toluenesulfonate, acetate, trifluoroacetate, mandelate, tartrate, and lactate. Preferable are free dihydrosphingosine, and hydrochloride thereof.

The dihydrosphingosine represented by formula (3) can be synthesized by an existing method. For example, the dihydrosphingosine can be produced by reducing a (2R,3R)-2-acetamino-3-hydroxyalkanoic acid ester with sodium borohydride, and then hydrolyzing the reduction product, in accordance with JP 3797695B.

Next, reaction conditions are described.

The amount of dihydrosphingosine may generally be 1 equivalent or more, preferably 1 to 10 equivalents, and more preferably 1 to 3 equivalents, of the ω-acyloxy long-chain fatty acid derivative (2).

In the case that $R^1$ is hydrogen in the present reaction, an activator is preferably also used for promoting the reaction.

Examples of the activator include acid chlorides such as pivalic acid chloride, isobutyloyl chloride, isopropyloyl chloride, trichloroacetic acid chloride, and acetyl chloride; chloroformates such as methyl chloroformate, t-butyl chloroformate, isobutyl chloroformate, and isopropyl chloroformate; sulfonic acid chlorides such as methanesulfonyl chloride, p-toluenesulfonyl chloride, and benzenesulphonyl chloride; and carbodiimides such as DCC(N,N-dicyclohexylcarbodiimide), EDC (1-ethyl-3-(3-dimethylaminopropyl) carbodiimide), and EDC hydrochloride.

The amount of activator may generally be 1 equivalent or more, preferably 1 to 10 equivalents, and more preferably 1 to 5 equivalents, of the ω-acyloxy long-chain fatty acid derivative (2).

In the case of using a carbodiimide as an activator, an additive generally used in the peptide synthesis, such as 1-hydroxybenzotriazole (HOBt), N-hydroxysuccinimide (HOSu), or 1-hydroxy-7-azabenzotriazole (HOAt), may also be used.

The amount of additive may generally be 1 equivalent or more, preferably 1 to 10 equivalents, and more preferably 1 to 5 equivalents, of the ω-acyloxy long-chain fatty acid derivative (2).

In the present reaction, a base is preferably also used for promoting the reaction.

The base to be used may be an inorganic base or an organic base.

Examples of the inorganic base include metal hydroxides such as sodium hydroxide, potassium hydroxide, lithium hydroxide, magnesium hydroxide, and barium hydroxide; and carbonates such as sodium carbonate, potassium carbonate, and sodium hydrogencarbonate.

The organic base is preferably a tertiary amine.

Examples of the tertiary amine include C1 to C12 trialkylamines such as trimethylamine, triethylamine, and ethyldiisopropylamine; tertiary amines containing a C1 to C4 alkyl group and a phenyl group, such as N,N-dimethylaniline, N,N-diethylaniline, and N,N-dimethylaminopyridine; nitrogen-containing organic bases such as pyridine, picoline, and lutidine; and C1 to C10 N,N,N,N-tetramethyl-α,ω-alkyldiamines such as N,N,N,N-tetramethyl-1,2-ethylenediamine, N,N,N,N-tetramethyl-1,3-propanediamine, and N,N,N,N-tetramethyl-1,6-hexanediamine. Each of these amines may be used alone, or two or more of these may be used in combination. In terms of economical efficiency, triethylamine is particularly preferable.

The amount of base may generally be 1 equivalent or more, preferably 1 to 10 equivalents, and more preferably 1 to 5 equivalents, of the ω-acyloxy long-chain fatty acid derivative (2).

Any reaction solvent may be used for the reaction, and examples thereof include polar aprotic solvents such as N,N-dimethylformamide (DMF), dimethyl sulfoxide (DMSO), N-methylpyrrolidone, and hexamethylphosphoric triamide; hydrocarbon solvents such as hexamethylbenzene, toluene, n-hexane, and cyclohexane; ether solvents such as diethyl ether, tetrahydrofuran (THF), diisopropyl ether, methyl tert-butyl ether, and dimethoxyethane; halogenated solvents such as chlorobenzene, methylene chloride, chloroform, and 1,1,1-trichloroethane; ester solvents such as ethyl acetate and butyl acetate; nitrile solvents such as acetonitrile and butyronitrile; alcohols such as methanol, ethanol, isopropanol, butanol, and octanol; and water. Each of these solvents may be used alone, or two or more of these may be used in combination. Among these, halogenated solvents having high solubility for the ω-acyloxy long-chain fatty acid derivative (2) are preferable, and chlorobenzene is more preferable.

The reaction temperature is generally in the range of −20° C. to 120° C., preferably −10° C. to 80° C., and more preferably 0° C. to 80° C.

After the reaction, a general work-up process may be performed in order to obtain a product from the reaction mixture. For example, water or the like is added to the reaction mixture after completion of the reaction, and then extraction is performed with use of a common extraction solvent such as ethyl acetate, diethyl ether, methylene chloride, toluene, or hexane. The reaction solvent and the extraction solvent are removed from the obtained extract by an operation such as heating under reduced pressure, and thereby the desired compound can be obtained. Alternatively, after completion of the reaction, the reaction solvent may be first removed by an operation such as heating under reduced pressure, followed by the above procedure.

The desired compound obtained by the above-mentioned method is almost pure, and may be further purified by a general method such as crystallization purification, fractional distillation, or column chromatography, for a higher purity.

The product may alternatively be recovered by a method of adding a poor solvent, such as hexane, to the reaction mixture, and then directly cooling the mixture for crystallization, without the above post treatment.

When applied, the thus synthesized novel type I natural ceramide derivative may be incorporated into a composition such as an external preparation for skin (e.g. moisturizer, cosmetic, etc.)

The novel type I natural ceramide derivative may be incorporated alone or in combination with at least one other ceramide into a composition such as an external preparation for skin.

In the case that a ceramide is incorporated into a composition such as an external preparation for skin, the composition is generally used in the form of a ceramide-containing emulsion. Ceramides, however, are a compound having high crystallinity and a high melting point of generally 100° C. or higher. Ceramides also have a specific amphiphilic structure, and therefore have a very low solubility in most of oil-soluble and/or water-soluble materials. Accordingly, preparation of a ceramide-containing emulsion has been difficult, and even if the emulsion is prepared, the emulsion has a problem of low stability which results, for example, in crystallization of ceramides after long-time storage. The present inventors have now found that blending a small amount of the novel type I natural ceramide derivative according to the present invention with other ceramides significantly improves the compatibility of the ceramides and thus enables easy emulsification and formulation.

The other ceramides are not particularly limited, and examples thereof include type II to type VII natural ceramides, ceramides of plant origin, and pseudoceramides.

The type II to type VII natural ceramides are compounds in which sphingosine, dihydrosphingosine, phytosphingosine, or sphingadienine is amidated. Specific examples thereof include compounds described in, for example, Journal of Lipid Research 1983, 24, 759; Journal of Lipid Research 1994, 35, 2069; and JP 2007-191443 A.

Examples of commercially available natural ceramides include Ceramide I, Ceramide III, Ceramide IIIA, Ceramide IIIB, Ceramide IIIC, Ceramide VI (products of Cosmoferm), Ceramide TIC-001 (product of Takasago International Corporation), and Ceramide II (product of Quest International).

Examples of the ceramides of plant origin include ceramides of wheat origin, konjac origin, soybean origin, corn origin, fungal origin, and rice origin.

The pseudoceramides are not particularly limited, and examples thereof include hydroxyethyl palmityl oxyhydroxypropyl palmitamide (Ceramide SL), trihydroxy palmitamide hydroxypropyl myristyl ether (Ceramide H03), N-(hexadecyloxyhydroxypropyl)-N-hydroxyethyl decanamide, and N-(hexadecyloxyhydroxypropyl)-N-hydroxyethyl hexadecanamide.

Among the ceramides, natural ceramides are preferable, type II natural ceramides and type III natural ceramides are more preferable, and type II natural ceramides are most preferable. Each of these other ceramides may be used alone, or two or more of these may be used in admixture.

The proportion of other ceramides may be freely determined. The weight ratio of the novel type I natural ceramide derivative to other ceramides is preferably in the range of 0.1:99.9 to 50.0:50.0, more preferably 1.0:99.0 to 20.0:80.0, and particularly preferably 5.0:95.0 to 20.0:80.0.

When blending the ceramides with one another, any material generally used for preparing products such as cosmetics may be used. Examples thereof include lower alcohols such as methanol, ethanol, isopropanol, and n-butanol; higher alcohols such as isostearyl alcohol, cetanol, stearyl alcohol, oleyl alcohol, and behenyl alcohol; polyhydric alcohols such as glycerin and 1,3-butanediol; long-chain fatty acids such as stearic acid, isostearic acid, palmitic acid, and lanolin acid; lower esters, higher esters, and polyhydric alcohol esters of the long-chain fatty acids; and hydrocarbons such as paraffin, liquid paraffin, and squalane. Among these, lower alcohols, higher alcohols, long-chain fatty acids, and long-chain fatty acid esters are preferable. Each of these materials may be used alone, or two or more of these may be used in combination. It is to be appreciated that ingredients other than the above materials may be further incorporated.

The amount of material used for blending the ceramides may be appropriately set according to the purpose, and the material may be used in any proportion. The amount of material is preferably 1 to 100000 times, and more preferably 1 to 10000 times the weight of the novel type I natural ceramide derivative.

The temperature at the time of blending is not particularly limited. Generally, the temperature is preferably 100° C. or lower, and more preferably 90° C. or lower, for blending without any special equipment.

The addition order and the like conditions may be appropriately determined according to the kind of the material to be used.

EXAMPLES

Hereinafter, the present invention will be described in more detail with reference to Examples. The present invention is not limited to these Examples.

Comparative Examples 1 to 5

Compatibility Test

A type II natural ceramide and a material were mixed at a weight ratio of 50:50 in a test tube, and the mixture was stirred in a constant-temperature bath at 70° C. After 20 minutes, the mixture was visually observed to determine whether the contents were in solution or not. The same test was then performed in the constant-temperature bath at 75° C., 80° C., 85° C., 90° C., 95° C., and 100° C. Table 1 shows the results.

Examples 1 to 5

Compatibility Test

A type II natural ceramide (TIC-001, product of Takasago International Corporation), a novel type I natural ceramide produced in the following Example 6, and a material were mixed at a weight ratio of 45:5:50 in a test tube, and the mixture was stirred in a constant-temperature bath at 70° C. After 20 minutes, the mixture was visually observed to determine whether the contents were in solution or not. The same test was then performed in the constant-temperature bath at 75° C., 80° C., 85° C., 90° C., 95° C., and 100° C. Table 1 shows the results.

TABLE 1

| Entry | Material | Weight ratio in mixture Type II natural ceramide:Novel type I natural ceramide:Material | Bath temperature (+: soluble, −: insoluble) | | | | | | |
|---|---|---|---|---|---|---|---|---|---|
| | | | 70° C. | 75° C. | 80° C. | 85° C. | 90° C. | 95° C. | 100° C. |
| Comparative Example 1 | Palmitic acid | 50:0:50 | − | − | − | − | + | + | + |
| Example 1 | Palmitic acid | 45:5:50 | − | + | + | + | + | + | + |
| Comparative Example 2 | nBuOH | 50:0:50 | − | − | − | − | + | + | + |
| Example 2 | nBuOH | 45:5:50 | − | + | + | + | + | + | + |
| Comparative Example 3 | Ethyl stearate | 50:0:50 | − | − | − | − | − | − | − |
| Example 3 | Ethyl stearate | 45:5:50 | − | − | − | − | − | + | + |
| Comparative Example 4 | Oleyl alcohol | 50:0:50 | − | − | − | − | + | + | + |
| Example 4 | Oleyl alcohol | 45:5:50 | − | − | + | + | + | + | + |

| Entry | Material | Weight ratio in mixture Type II natural ceramide:Novel type I natural ceramide:Material) | Bath temperature (+: soluble, −: insoluble) | | | | | | |
|---|---|---|---|---|---|---|---|---|---|
| | | | 70° C. | 75° C. | 80° C. | 85° C. | 90° C. | 95° C. | 100° C. |
| Comparative Example 5 | Squalane | 50:0:50 | − | − | − | − | − | − | − |
| Example 5 | Squalane | 45:5:50 | − | − | − | − | − | + | + |

The results show that blending the novel type I natural ceramide with the type II natural ceramide improved the compatibility of the ceramides and decreased the melting point of the mixture.

Example 6

Method for Producing Novel Type I Natural Ceramide

A chlorobenzene (3 mL) suspension containing 30-stearoyloxytriacontanoic acid (70 mg, 0.095 mmol), dihydrosphingosine hydrochloride (48.2 mg, 0.243 mmol), triethylamine (28.8 mg, 0.285 mmol), 1-hydroxybenzotriazole (HOBt) (35.9 mg, 0.266 mmol), and 1-ethyl-3-(3-dimethylaminopropyl) carbodiimide (EDC) (17.4 mg, 0.143 mmol) was stirred while being heated for six hours at a bath temperature of 40° C. Then, 2-propanol (3 mL) was added to the reaction mixture at the same temperature, and the mixture was left to cool so that the internal temperature thereof would be 21° C. From the mixture, a solid was recovered by filtration, and then the solid was dried under reduced pressure (40° C./1 mmHg), whereby the desired compound was produced (86.6 mg, yield: 89.5%).
$^1$H NMR (400 MHz, CDCl$_3$:CD$_3$OD=4:1/ppm): δ 0.88 (t, 6H), 1.11-1.31 (m, 104H), 1.51-1.64 (m, 8H), 2.22 (t, 2H), 2.33 (t, 2H), 3.63-3.69 (m, 2H), 3.77-3.86 (m, 2H), 4.06 (t, 2H).

The invention claimed is:

1. A novel type I natural ceramide derivative represented by formula (1):

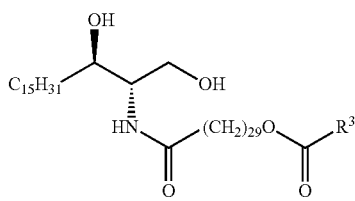

(1)

wherein R$^3$ represents a substituted or unsubstituted C1 to C30 alkyl group, or a substituted or unsubstituted C7 to C20 aralkyl group.

2. A composition comprising the novel type I natural ceramide derivative according to claim 1.

3. The composition according to claim 2, further comprising at least one other ceramide.

4. The composition according to claim 3, wherein a weight ratio of the novel type I natural ceramide derivative to the at least one other ceramide is 1:99 to 20:80.

5. The composition according to claim 4, wherein the weight ratio of the novel type I natural ceramide derivative to the at least one other ceramide is 5:95 to 20:80.

6. The composition according to claim 3, wherein the at least one other ceramide is a natural ceramide.

7. The composition according to claim 6, wherein the natural ceramide is a type II natural ceramide and/or a type III natural ceramide.

8. The composition according to claim 7, wherein the natural ceramide is a type II natural ceramide.

9. An external preparation for skin, comprising the composition according to claim 2.

10. A moisturizer comprising the composition according to claim 2.

11. A method for producing the novel type I natural ceramide derivative according to claim 1, comprising
reacting an ω-acyloxy long-chain fatty acid derivative represented by formula (2):

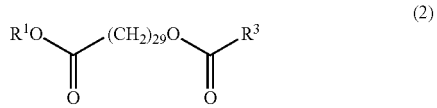

(2)

wherein R$^1$ represents a substituted or unsubstituted C1 to C18 alkyl group, a substituted or unsubstituted C6 to C20 aryl group, a substituted or unsubstituted C7 to C20 aralkyl group, or hydrogen, and R$^3$ represents a substituted or unsubstituted C1 to C30 alkyl group, or a substituted or unsubstituted C7 to C20 aralkyl group,
with dihydrosphingosine represented by formula (3):

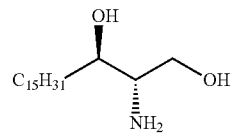

(3)

or a salt thereof.

12. The composition according to claim 4, wherein the at least one other ceramide is a natural ceramide.

13. The composition according to claim 5, wherein the at least one other ceramide is a natural ceramide.

14. An external preparation for skin, comprising the composition according to claim 3.

15. An external preparation for skin, comprising the composition according to claim 4.

16. An external preparation for skin, comprising the composition according to claim 5.

17. An external preparation for skin, comprising the composition according to claim 6.

18. An external preparation for skin, comprising the composition according to claim 7.

19. An external preparation for skin, comprising the composition according to claim 8.

20. A moisturizer comprising the composition according to claim 3.

\* \* \* \* \*